Figure 1:
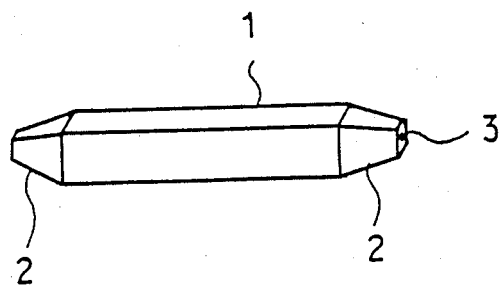

United States Patent [19]
Ikada et al.

[11] Patent Number: 4,898,186
[45] Date of Patent: Feb. 6, 1990

[54] OSTEOSYNTHETIC PIN

[75] Inventors: Yoshito Ikada; Hyu H. Suong; Yoshihiko Shimizu, all of Uji; Satoshi Watanabe; Tatsuo Nakamura, both of Kyoto; Masakazu Suzuki, Ayabe; Takeshi Shimamoto, Nagaokakyo, all of Japan

[73] Assignee: Gunze Limited, Ayabe, Japan

[21] Appl. No.: 199,412

[22] PCT Filed: Sep. 11, 1987

[86] PCT No.: PCT/JP87/00673
§ 371 Date: Apr. 29, 1988
§ 102(e) Date: Apr. 29, 1988

[87] PCT Pub. No.: WO88/01849
PCT Pub. Date: Mar. 24, 1988

[30] Foreign Application Priority Data
Sep. 11, 1986 [JP] Japan ............................ 62-215077

[51] Int. Cl.⁴ .......................... A61F 5/04; A61F 2/28
[52] U.S. Cl. .................................. 606/62; 623/16; 264/164; 606/77

[58] Field of Search .............. 623/16, 66; 128/92 YR, 128/92 YP, 92 Y, 92 YZ, 92 ZW; 264/164, 231

[56] References Cited

U.S. PATENT DOCUMENTS

| 4,506,681 | 3/1985 | Mundell | 623/16 X |
| 4,550,449 | 11/1985 | Tunc | 623/16 |
| 4,650,488 | 3/1987 | Bays et al. | 623/66 X |
| 4,781,183 | 11/1988 | Casey et al. | 623/16 X |

FOREIGN PATENT DOCUMENTS

| 48-42439 | 12/1973 | Japan . |
| 61-41466 | 2/1986 | Japan . |
| 61-135671 | 6/1986 | Japan . |
| 61-193666 | 8/1986 | Japan . |

Primary Examiner—Alan W. Cannon
Attorney, Agent, or Firm—Armstrong, Nikaido, Marmelstein, Kubovcik & Murray

[57] ABSTRACT

An osteosynthetic pin characterized in that the pin is formed substantially of a poly-L-lactic acid having a molecular weight of at least about 70,000, and is formed by axially drawing about 2 to about 10 times at an elevated temperature of about 70° to about 120° C.

6 Claims, 1 Drawing Sheet

OSTEOSYNTHETIC PIN

TECHNICAL FIELD

The present invention relates to bone fixing pins for use in surgery, especially for use with cut ribs, fractured bones or the like for fixing and remedying the bones.

BACKGROUND ART

Metal or alumina ceramic osteosynthetic pins have heretofore been used clinically for remedying cut or fractured bones by inserting the pin into the marrow cavity of the cut or fractured bone and fixing the bone.

However, these osteosynthetic pins have the disadvantages of being low in elasticity, exerting no shock-absorbing action relative to the movement of the fixed bone portion and stimulating the bone to cause an inflammation or retard osteogenesis. Moreover, they have poor affinity for the living body, are not absorbable by the living body and therefore have the problem of permanently remaining in the living body after the fracture has been remedied, possibly causing contamination with bacteria or an inflammation.

DISCLOSURE OF THE INVENTION

An object of the present invention is to provide an osteosynthetic pin having suitable elasticity and high affinity for the living body, absorbable by the living body after surgery and advantageously usable in regenerating and remedying the bone without causing an inflammation to the fixed portion and further without entailing the objection that could result if the pin remains permanently in the living body.

Another object of the invention is to provide an osteosynthetic pin capable of exhibiting an osteogenesis promoting effect on fixed bones.

The osteosynthetic pin of the present invention is characterized in that the pin is formed substantially of a poly-L-lactic acid having a molecular weight of at least about 70,000.

We have conducted research on various high-molecular-weight substances having affinity for living body and absorbable by the living body to explore whether these substances are usable for osteosynthetic pins. Many of the high-molecular-weight substances investigated did not have suitable elasticity required of osteosynthetic pins, were low in initial strength or failed to retain the required strength during the bone regeneration period (usually about 2 months), and were therefore unsuited to use for osteosynthetic pins. Nevertheless, we have found that of the homopolymers of L-lactic acid, only poly-L-lactic acid having a molecular weight of at least 70,000 is excellent in initial strength, retains the required strength during the bone regeneration period, permits effective regeneration and remedy of bones and is therefore very suitable for osteosynthetic pins. Moreover, the poly-L-lactic acid posseses suitable elasticity, accordingly exhibits a shock-absorbing action relative to the movement of the fixed bone portion and is unlikely to cause an inflammation or retard regeneration of bones by stimulating bones. The poly-L-lactic acid further has excellent affinity for the intramedullary tissue when placed into the marrow cavity and is gradually absorbed by the living body through hydrolysis therein, so that the acid is usable free of the objection that would result if the acid remains permanently in the living body like metal or alumina ceramics.

Although the poly-L-lactic acid to be used in the present invention is itself known, no report has been made on the acid as used for osteosynthetic pins. Homopolymers of L-lactic acid which are less than about 70,000 in molecular weight are not satisfactory in the properties required of osteosynthetic pins, i.e. in initial strength and strength retentivity during the bone regeneration period, and are not usable for the pin. The poly-L-lactic acid suited to the present invention is at least about 70,000, more preferably at least about 100,000 and most preferably at least 150,000, in molecular weight. The upper limit of the molecular weight, although not limited specifically, is generally about 150,000 in view of shapability, etc.

The molecular weight of the poly-L-lactic acid mentioned herein is determined by dissolving the acid in chloroform to a concentration of 0.2 g/dl, further diluting the solution to determine the intrisinc viscosity $[\eta]$, and calculating the viscosity average molecular weight from the following equation.

$$[\eta] = KM^\alpha$$

$$\left( \begin{array}{l} K = 5.45 \times 10^{-4} \\ \alpha = 0.73 \end{array} \right)$$

To give the osteosynthetic pin increased affinity to the living body and enable the pin to exhibit a bone regeneration promoting effect when fixing bones, it is desirable to use the poly-L-lactic acid with hydroxyapatite (hereinafter referred to as "HAP") admixed therewith. HAP is a known substance in the form of inorganic crystals represented by the formula $Ca_{10}(PO_4)_6(OH)_2$. According to the invention, HAP is used in the form of particles, preferably about 1 μm to about 100 μm in diameter, as uniformly admixed with the poly-L-lactic acid, usually in an amount of about 1 to about 15 wt. %, preferably about 5 to about 10 wt. %, based on the poly-L-lactic acid. HAP can be admixed with the lactic acid by any desired method, for example, by mixing the two materials together in the form of powders, or by uniformly mixing HAP with a solution of the lactic acid polymer and evaporating off the solvent from the mixture. Further to assure promoted regeneration of the bone and improved strength, calcium phosphate fiber obtained from HAP can be admixed with the poly-L-lactic acid for preparing the pin of the invention.

Figure 2:
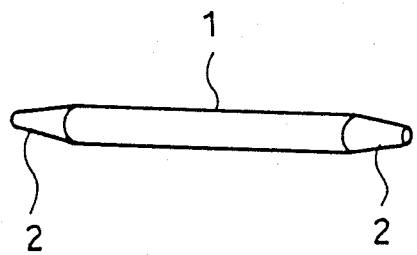

The present osteosynthetic pin can be of any desired shape, for example, in the form of a plate, polygonal prism (such as quadrangular, pentagonal, hexagonal or octagonal prism), solid cylinder or the like. For example, the pin can be in the form of a plate or polygonal prism which is about 2 to about 7 mm in thickness, about 2 to about 7 mm in width and about 20 to about 50 mm in length, or a solid cylinder about 3 to about 7 mm in diameter and about 20 to about 50 mm in length. With reference to the accompanying drawings showing preferred examples of osteosynthetic pins embodying the invention, FIG. 1 is a perspective view showing an osteosynthetic pin in the form of a plate, and FIG. 2 is a perspective view showing an osteosynthetic pin in the form of a solid cylinder.

Referring to these drawings, the pin 1 of the invention has tapered opposite ends 2, which are desirable for facilitating the insertion of the pin into the marrow cavity of the bone. Indicated at 3 in FIG. 1 is a bore which extends through the pin axially thereof and which is formed when desired. When provided, the bore achieves an enhanced curing effect without impeding the growth of myeloid cells.

The osteosynthetic pin of the present invention is prepared by shaping the poly-L-lactic acid, or a mixture of the acid and HAP. The poly-L-lactic acid has excellent shapability at a relatively low temperature and therefore readily affords osteosynthetic pins in a desired shape. The pin is produced, for example, by shaping the material at an elevated temperature of not lower than the melting point of the poly-L-lactic acid using a hot press, or by extruding the material from a nozzle of suitable orifice diameter at a temperature of not lower than the melting point, drawing the extrudate axially thereof and, when required, tapering the resulting piece. The axial drawing gives improved elasticity and strength to the pin. The extrudate is drawn at an elevated temperature usually of about 70° to about 120° C., preferably about 2 to about 10 times axially.

The osteosynthetic pin of the invention is inserted into the marrow cavity of a cut or fractured bone to fix and remedy the bone. The pin is advantageously usable for remedying fractured or out ribs and also for fixing and remedying fractured or cut bones in various body portions.

The features of the invention will be made apparent from the following examples of the invention.

EXAMPLES

Example 1

A powder of poly-L-lactic acid, about 123,000 in molecular weight, was held in a hot press at 200° C. for 5 minutes free of any pressure to melt the lactic acid, and the melt was then held at the same pressure for 5 minutes under a pressure of 200 kg/cm$^2$ and thereafter cooled rapidly to obtain a 3-mm-thick plate of poly-L-lactic acid. Rib fixing pins having the shape shown in FIG. 1, a width of 6 mm and a length of 40 mm were prepared from the plate by cutting.

The rib fixing pins were immersed in a phosphate buffer (PBS) containing 0:9 wt. % of sodium chloride at 37° C. for a hydrolysis test to determine the relationship between the immersion period and weight, bending strength or bending Young's modulus. Table 1 shows the results.

TABLE 1

| Item | Initial | Immersion period | | | |
|---|---|---|---|---|---|
| | | 1 Month | 2 Months | 3 Months | 6 Months |
| Weight retentivity (%) | 100 | 100 | 100 | 100 | 100 |
| Bending strength (kg/mm$^2$) | 11.1 | 11.2 | 12.6 | 11.4 | 3.7 |
| Bending strength retentivity (%) | 100 | 101 | 114 | 102 | 33 |
| Bending Young's modulus (kg/mm$^2$) | 288 | 296 | 319 | 314 | 289 |
| Bending Young's modulus retentivity (%) | 100 | 103 | 111 | 109 | 100 |

The bending strength and bending Young's modulus were measured according to JIS K7203. The weight retentivity, bending strength retentivity and bending Young's modulus retentivity are expressed in percentage relative to the respective initial values.

Example 2

Poly-L-lactic acid, about 72,000 in molecular weight, was dissolved in methylene chloride, 5 wt. % of hydroxyapatite (proportions by weight of main components: 55.8% CaO, 42.3% P$_2$O$_5$ and 0.3% MgO; particle size up to 0.088 mm) was added to the solution, the mixture was stirred and the solvent was removed from the mixture to obtain a homogeneous material containing hydroxyapatite. The material was shaped into a plate by a hot press, and the plate was then drawn two times in hot water at 80° C. and made into osteosynthetic pins each in the form of a solid cylinder, 2 mm in diameter and 20 mm in length.

The pins were 16.2 kg/mm$^2$ in initial bending strength and retained 80% of the initial strength after having been tested in vitro as immersed in PBS for 2 months.

Seven hybrid adult dogs (weighing 7 to 15 kg) were intramusculary anesthetized with 10 mg/kg of Ketaral and 0.1 mg/kg of Rompun and subject to mechanical ventilation under positive pressure while intubated with a tracheal tube to perform the following surgery using some of the pins of the present example and osteosynthetic stainless steel pins for comparison.

The left 9th, 10 and 11th ribs were cut inclusive of the periosteum at a site about 2 to about 4 cm from the costal angle, and the cylindrical pin was inserted into the marrow cavity of each rib to join the cut rib at the site. The rib was tied with #7 silk ligature at a proximal site and a distal site each at a distance of 1.5 cm from the cut end, and the tied pieces of ligature were tied to each other to fix the joined portion. The fixed portion was thereafter checked for a cure from time to time by X-ray examination, and the fixed portion was removed en bloc 2 weeks, 3 weeks, 1 month, 2 months or 3 months after the surgery to check the rib for tissue reaction and also check the material for a change.

Consequently, the osteosynthetic pin of poly-L-lactic acid was found to exhibit high affinity for the living body, and the bone was found to have been completely fixed one month after the surgery. On the other hand, the stainless steel pin exhibited poor affinity for the intramedullary tissues and was found to have been surrounded by a connective tissue layer. At the portion where the pin was in direct contact with the bone, the bone became thin, permitting the pin to slip off in some cases.

Example 3

To 100 parts by weight of a powder of poly-L-lactic acid, about 72,000 in molecular weight, was added 5 parts by weight of the same hydroxyapatite as used in Example 2, and the mixture was thoroughly stirred and then extruded into a rod from a nozzle having a single orifice with a diameter of 3 mm at a temperature of 230° C. using a single-screw spinning machine. The rod of poly-L-lactic acid containing hydroxyapatite was axially drawn two times in air at about 80° C. and thereafter cut into pieces having a length of 40 mm. Each of the pieces was tapered at its opposite ends to obtain a rib fixing pin as shown in FIG. 2.

The osteosynthetic pins thus prepared had the strength shown in Table 2 below, which also shows the strength of the rod before the drawing.

TABLE 2

|  | Before drawing | After drawing |
| --- | --- | --- |
| Bending strength (kg/mm$^2$) | 11.2 | 16.2 |
| Bending Young's modulus (kg/mm$^2$) | 184 | 462 |

Some of the rib fixing pins were subjected to a hydrolysis test (hereinafter referred to as an "in vitro test") in a phosphate buffer (PBS) containing 0.9 wt. % of sodium chloride. Table 3 shows the results.

TABLE 3

| | | | Immersion period | | | |
| --- | --- | --- | --- | --- | --- | --- |
| | | | | Months | | |
| Item | Initial | 2 Weeks | 1 | 2 | 3 | 6 |
| Weight retentivity (%) | 100 | 100 | 100 | 100 | 100 | 98 |
| Bending strength (kg/mm$^2$) | 16.2 | 13.7 | 12.9 | 12.8 | 10.0 | 3.8 |
| Bending strength retentivity (%) | 100 | 85 | 80 | 79 | 62 | 24 |
| Bending Young's modulus (kg/mm$^2$) | 462 | 383 | 445 | 421 | 376 | 262 |
| Bending Young's modulus retentivity | 100 | 83 | 96 | 91 | 81 | 57 |

Next, cut ribs of adult dogs were fixed each with the pin and checked for fixation. Although the cut portion was not yet completely fixed two weeks thereafter, the rib fixing pin was found to have been firmly joined to the intramedullary tissue, thus satisfactory serving as an osteosynthetic pin.

For comparison, 2-cm-long cut pieces of Kirschner's wire, 2 mm in diameter, were tested in vivo in the same manner as above. Two weeks after the start of testing, the Kirschner's wire was found to be loosely positioned in the bone without joining to the intramedullary tissue in any way and was readily movable within the bone marrow when pressed on from outside the living body, thus stimulating the tissue and failing to serve as a fixing pin.

We claim:

1. An osteosynthetic pin obtained by shaping a poly-L-lactic acid having a molecular weight of at least about 70,000 and axially drawing the shaped body about 2 to about 10 times at an elevated temperature of about 70° to about 120° C.

2. An osteosynthetic pin as defined in claim 1 wherein the poly-L-lactic acid has a molecular weight of at least about 100,000.

3. An osteosynthetic pin as defined in claim 1 wherein the poly-L-lactic acid contains about 1 to about 15 wt % of hydroxyapatite admixed with the poly-L-lactic acid.

4. An osteosynthetic pin as defined in claim 3 wherein the content of hydroxyapatite is in the range of about 5 to about 10 wt %.

5. An osteosynthetic pin as defined in claim 1 or 3 further comprising a bore extending axially through the pin.

6. A process for preparing an osteosynthetic pin, omprising: shaping a poly-L-lactic acid having a molecular weight of at least about 70,000 and axially drawing the shaped body about 2 to about 10 times at an elevated temperature of about 70° to about 20° C.

* * * * *